US005925029A

United States Patent [19]

Jansen et al.

[11] Patent Number: 5,925,029

[45] Date of Patent: Jul. 20, 1999

[54] METHOD AND APPARATUS FOR FIXING A CONNECTOR ASSEMBLY ONTO A VIAL WITH A CRIMP CAP

[75] Inventors: Hubert Jansen, Poisat; Jean Claude Thibault, Saint Egreve, both of France

[73] Assignee: Becton, Dickinson and Company, Franklin Lakes, N.J.

[21] Appl. No.: 08/937,638

[22] Filed: Sep. 25, 1997

[51] Int. Cl.$^{6}$ .................................................... A61B 19/00

[52] U.S. Cl. .......................... 604/411; 604/415; 604/403

[58] Field of Search ..................................... 604/403, 411, 604/412, 414, 415, 905; 141/319, 346, 347, 349, 351; 251/325, 333, 344, 347, 349, 353; 215/355, 247, 364

[56] References Cited

U.S. PATENT DOCUMENTS

| | | | |
|---|---|---|---|
| Re. 34,045 | 8/1992 | McFarland | 604/198 |
| 37,221 | 12/1862 | Dunton . | |
| 659,519 | 10/1900 | De Oliveira . | |
| 2,607,503 | 8/1952 | Sonnenberg | 215/38 |
| 2,667,986 | 2/1954 | Perelson | 215/48 |
| 2,953,132 | 9/1960 | Richter et al. | 128/272 |
| 3,164,303 | 1/1965 | Trautmann | 222/190 |
| 3,206,080 | 9/1965 | Scislowicz | 222/383 |
| 3,356,093 | 12/1967 | Monahon | 128/349 |
| 3,357,427 | 12/1967 | Wittke et al. | 128/235 |
| 3,674,028 | 7/1972 | Ogle | 128/272 |
| 3,779,371 | 12/1973 | Rovinski | 206/47 |
| 3,838,689 | 10/1974 | Cohen | 128/218 |
| 4,020,839 | 5/1977 | Klapp | 128/272 |
| 4,048,999 | 9/1977 | Köbel | 128/272.1 |
| 4,153,057 | 5/1979 | Köbel | 128/272.1 |
| 4,187,893 | 2/1980 | Bujan | 150/8 |
| 4,210,255 | 7/1980 | Pan | 220/209 |
| 4,336,891 | 6/1982 | Smith | 215/276 |
| 4,387,879 | 6/1983 | Tauschinski | 251/149.1 |
| 4,412,623 | 11/1983 | Schmidt | 215/11 R |
| 4,418,827 | 12/1983 | Butterfield | 215/247 |
| 4,425,120 | 1/1984 | Sampson et al. | 604/198 |
| 4,573,506 | 3/1986 | Paoletti | 141/98 |
| 4,573,976 | 3/1986 | Sampson et al. | 604/198 |
| 4,576,211 | 3/1986 | Valentini et al. | 141/329 |
| 4,672,996 | 6/1987 | Floyd et al. | 137/522 |
| 4,792,053 | 12/1988 | Towns et al. | 215/250 |
| 4,822,351 | 4/1989 | Purcell | 604/411 |
| 4,826,491 | 5/1989 | Schramm | 604/198 |
| 4,834,149 | 5/1989 | Fournier et al. | 141/1 |
| 4,834,152 | 5/1989 | Howson et al. | 141/286 |
| 4,850,994 | 7/1989 | Zerbst et al. | 604/198 |

(List continued on next page.)

FOREIGN PATENT DOCUMENTS

| | | | |
|---|---|---|---|
| 0 065 469 | 11/1982 | European Pat. Off. . |
| 0 236 127 A2 | 9/1987 | European Pat. Off. . |
| 0 406 374 B1 | 8/1993 | European Pat. Off. . |
| 1 487 413 | of 0000 | France . |
| 950 625 | 10/1949 | France . |
| 1 071 487 | 9/1954 | France . |
| 36 18 158 A1 | 12/1987 | Germany . |
| 2 738 550 | 9/1997 | Germany . |
| 501 172 | 2/1971 | Switzerland . |
| 2 121 016 | 12/1983 | United Kingdom . |
| WO 95/03841 | 2/1995 | WIPO . |
| WO 97/39720 | 10/1997 | WIPO . |

*Primary Examiner*—Robert A. Clarke
*Assistant Examiner*—David J. Cho
*Attorney, Agent, or Firm*—Allen W. Wark

[57] ABSTRACT

A method and apparatus for attaching a connector assembly onto a vial is disclosed. The connector assembly features a protective cap, a collar attachable to the rim of the vial, and a crimp cap for securing the collar to the rim. A vial access device is contained within the collar. One or more ribs are provided adjacent a distal portion of the collar to seal against the stopper obturating the vial. The collar is provided with one or more slits which render the collar flexible in directions radial and axial to the central axis of the vial to compensate for variations in tolerances or dimensions present in the various components. The crimp cap can be supplied preattached to the collar in an uncrimped condition.

10 Claims, 11 Drawing Sheets

U.S. PATENT DOCUMENTS

| | | | |
|---|---|---|---|
| 4,884,703 | 12/1989 | O'Meara | 215/6 |
| 4,909,290 | 3/1990 | Coccia | 141/329 |
| 4,923,447 | 5/1990 | Morgan | 604/198 |
| 5,006,118 | 4/1991 | Yule | 604/408 |
| 5,088,996 | 2/1992 | Kopfer et al. | 604/415 |
| 5,116,326 | 5/1992 | Schmidt | 604/198 |
| 5,171,214 | 12/1992 | Kolber et al. | 604/82 |
| 5,215,538 | 6/1993 | Larkin | 604/249 |
| 5,217,433 | 6/1993 | Bunin | 604/89 |
| 5,232,109 | 8/1993 | Tirrell et al. | 215/247 |
| 5,291,991 | 3/1994 | Meyer | 206/221 |
| 5,348,548 | 9/1994 | Meyer et al. | 604/403 |
| 5,352,196 | 10/1994 | Haber et al. | 604/90 |
| 5,358,501 | 10/1994 | Meyer | 604/414 |
| 5,360,413 | 11/1994 | Leason et al. | 604/249 |
| 5,385,546 | 1/1995 | Kriesel et al. | 604/85 |
| 5,423,791 | 6/1995 | Bartlett | 604/403 |
| 5,425,465 | 6/1995 | Healy | 215/355 |
| 5,429,256 | 7/1995 | Kestenbaum | 215/247 |
| 5,487,737 | 1/1996 | Meyer | 604/403 |
| 5,494,170 | 2/1996 | Burns | 215/247 |
| 5,520,661 | 5/1996 | Lal et al. | 604/246 |
| 5,533,983 | 7/1996 | Haining | 604/249 |
| 5,533,994 | 7/1996 | Meyer | 604/416 |
| 5,566,729 | 10/1996 | Grabenkort et al. | 141/25 |
| 5,598,939 | 2/1997 | Watson et al. | 215/307 |
| 5,613,291 | 3/1997 | Solomon et al. | 29/458 |
| 5,620,434 | 4/1997 | Brony | 604/406 |
| 5,685,845 | 11/1997 | Grimard | 604/82 |
| 5,702,019 | 12/1997 | Grimard | 215/301 |

METHOD AND APPARATUS FOR FIXING A CONNECTOR ASSEMBLY ONTO A VIAL WITH A CRIMP CAP

FIELD OF THE INVENTION

The invention relates to a method and apparatus for fixing a connector assembly onto a vial, and more particularly, to a method and apparatus for fixing a connector assembly onto a vial which minimizes the number of components in the connector assembly and which reduces the number of microbial barriers necessary to safeguard sterility of the system.

BACKGROUND

In the art, it is generally known that to reduce inventory space or to increase the shelf life of certain drugs, or both, it is advantageous to reduce these drugs to a dry or powdered form. These dry or powdered drugs are normally stored in a sealed container such as a vial, and reconstituted into liquid form with an appropriate diluent or solvent solution prior to administration to a patient. The vials, typically formed of glass or plastic materials, include an elastomeric stopper sealing the open end of the vial. The stopper includes a portion inserted into the neck of the vial as well as a planar portion which rests on top of the vial, against the vial rim. The planar portion is normally tightly affixed to the vial rim with an aluminum crimp cap. Owing to the malleable nature of aluminum, the crimp cap readily adapts itself any differing dimension or tolerances which may exist between the stopper and the vial. The result is that the crimp cap evenly distributes sealing forces between the stopper and the vial. Thus, it has been generally recognized in the art that the vial/stopper/aluminum crimp cap solution safeguards the sterility of the drug contained within the vial over suitably long storage periods and prescribed conditions. The sizes and dimensions of the various vials and stopper components may be configured to given standards, such as given ISO standards.

One way to reconstitute the drug stored in the vial is to introduce the solvent or diluent from a syringe by piercing the stopper sealing the vial. Owing to various considerations, such as the convenience of the healthcare worker charged with reconstituting the drug, the art has recognized ways to transform the standard sealed vial into a system suitable for permitting safe, effective reconstitution of the drug contained within the vial. In these systems, typically, a fluid transfer assembly is connected to the neck of the vial. The fluid transfer system includes structure for connecting the vial to a source of diluent, such as diluent held in bottles, bags or syringes. The transfer assembly is thereafter activated to permit the flow of fluid into the vial to from the source of diluent, thereby reconstituting the drug.

In some configurations, the systems are such that standard vial stopper is eliminated in favor of fluid transfer assembly having a rubber stopper which is inserted into the neck of the vial, without the need for a planar portion which rests against the rim of the vial. This stopper remains within the neck until such time as reconstitution of the drug is desired. When the transfer assembly is activated, the stopper is urged towards the interior of the vial to open the neck, thereby permitting fluid to flow through the transfer assembly and into the vial body. Examples of such approaches include the MONOVIAL® line of drug delivery devices manufactured and sold by Becton Dickinson Pharmaceutical Systems of Le Pont de Claix, France and exemplified, for instance, by U.S. Pat. No. 5,358,501. While forming an excellent drug reconstitution system displaying superior properties, particularly convenience of use and sterility maintenance of the drug held in the vial, as typically configured these systems are useful for vial applications where the vial is of a relatively large size, typically 12 milliliters ("ml") or more. Accordingly, some pharmaceutical companies have expressed the desire for a reconstitution approach wgee the vial is of a size smaller than the sizes for which the aforementioned system is normally configured.

In response to the aforementioned concerns, then, one logical way around the dilemma would be to convert, as exactly as possible, the characteristics associated with vial components already in use by the pharmaceutical companies, such as ISO standard vial/stopper/aluminium crimp cap components, and to implement a reconstitution system around these components for use by the healthcare worker. The prior art has considered some attempts in that regard. For instance, as exemplified by PCT Patent Application No. WO 97/10156 to Biodome, SA of Issoire Cedex, France, the aluminum crimp cap which would normally hermetically affix the planar portion of the standard stopper to the vial rim is replaced by a rubber-piercing fluid transfer assembly affixed around the neck of the vial. This rubber piercing fluid transfer assembly is activated by an end user when it is desired to reconstitute the drug held in the vial. The transfer assembly disclosed in this patent application features a fairly rigid, outermost plastic locking ring which, in theory, should lock the plastic transfer assembly firmly against the planar portion of the stopper and, hence, sealing this portion stopper against the vial rim. As has been pointed out, though, in practice, there may be significant variance between the dimensional tolerances of the glass components (the vial), the rubber components (the stopper) and the plastic components (the fluid transfer assembly) forming the system. The malleable nature of the aluminum crimp cap takes into account differences in tolerances. However, owing to the rigid characteristics of the sealing ring, with this approach, there may be the possibility that given a particular vial, stopper, or transfer assembly, the sealing forces realized by the outside sealing ring against the stopper and the vial may not be sufficient or otherwise uniform. Accordingly, the potential contamination of the drug, given the environmental stresses to which the vial may be subject to during manufacture, shipping, or storage, presents a concern.

Accordingly, there is a need for a safe and effective drug reconstitution system, wherein a fluid transfer assembly is affixed to a standard vial and stopper arrangement in a manner such that the sealing forces achievable by an aluminum crimp cap are effectively replicated. Such a drug reconstitution system is disclosed herein.

SUMMARY OF THE INVENTION

The present invention addresses the aforementioned concerns in a convenient and cost-efficient manner. A connector assembly in accordance with the present invention is designed to be employed with a standard vial and stopper so as to be able to be processed by a pharmaceutical manufacturer with standard processing equipment. The connector assembly is fully able to account for dimensional variances or tolerance variances in the vial or stopper components or in the components forming the connector assembly itself, so as to ensure good microbiological barrier characteristics.

The connector assembly features a protective cap for covering the open end of the vial neck. The cap includes an open proximal end, a closed distal end, and a shield wall formed therebetween. A collar is provided adjacent the open proximal end of the cap. The collar can be molded with the cap, or it can be separately manufactured and thereafter affixed to the cap. The collar features a proximal end, a distal end, and a sidewall therebetween. One or more rib elements are provided on an interior portion of the collar adjacent the distal end, and the ribs designed to form a tight seal against the stopper as the collar is positioned against the stopper. Interior portions of the collar can be configured to mate with a vial access device provided to pierce the stopper. One or more deflectable latches are provided about the proximal end of the collar. Each of the latches includes locking means deflectable about the rim of the vial for securely attaching the collar to the vial.

A defining aspect of the collar is the provision of one or more slits or cuts in the sidewall. These slits or cuts are designed so as to permit the sidewall to flex in axial and radial directions respective of the neck of the vial. In this manner, the sidewall is rendered more flexible respective of the vial neck, allowing the collar to compensate for any dimensional or tolerance variances in the vial, the stopper, or in the connector assembly itself.

A crimp cap fixes the collar to the vial rim. As the collar is locked to the rim of the vial by the crimp cap, the collar is tightly thrust against the stopper, thereby ensuring a proper seal of the stopper to the vial. Additionally, the ribs provided in the internal portion of the collar form an additional microbiological barrier against the ambient environment. The crimp cap can be preaffixed to the collar in an uncrimped condition, with the crimping operation occurring after the collar is placed around the vial rim. Alternately, the crimp cap can be affixed about the collar after the collar is placed onto the vial rim.

The connector assembly can be shipped to a pharmaceutical manufacturer, eith with the crimp cap preaffixed or not. In the cleanroom environment where the vial is filled with a medicament and the stopper is placed against the rim, the connector assembly can be attached to the vial. The connector assembly is transferred from a first position, whereby the collar is placed around the rim and the distal end of the collar spaced from the stopper, to a second position, whereby the deflectable latches of the collar are thrust about the outside surface of the rim and against an underside portion of the rim. By this action also, the ribs provided in the interior of the collar are thrust into sealing relation with the stopper. Thereafter, the crimp cap is postioned in crimped relation about the the collar and the vial rim to secure the collar the vial rim. The crimp cap is thus thrust against the latches, securing the latches in place, and ensuring that the collar is securely locked to the vial. The slits provided in the sidewall of the collar allow the collar to compensate for any dimensional or tolerance variations present in the vial, the stopper, or in the connector assembly itself. If the crimp cap is supplied to the customer preattached to the collar but in an uncrimped state, the connector assembly itself is secured to the vial in sealing relation with the stopper within the cleanroom environment, and the crimping operation itself need only occur outside of the cleanroom.

If desired, the cap and collar can be manufactured in such a manner such that the cap is removable from the collar by a twisting action, permitting a user a convenient way to engage the vial access device held by the connector assembly. In one configuration, the cap can be formed with the collar with a frangible connection formed from a material—such as a thermoplastic elastomer—that is different from the material forming the cap and collar itself, such as polypropylene or polyethylene. The user may simply twist the cap such that the frangible connection shears, allowing the user to remove the cap from the collar to expose the vial access device. One way to achieve this construction is through a co-injection process. All in all, the minimization of the number of components forming the connector assembly results in a concomitant reduction in the number of biological barriers necessary to safeguard the sterility of the vial access device as well as the medicament contained within the vial.

BRIEF DESCRIPTION OF THE DRAWINGS

The invention will now be described in detail by way of reference to the appended drawings, wherein.

DETAILED DESCRIPTION OF THE PREFERRED EMBODIMENTS

A convention used throughout this application is that the term "proximal" denotes a distance closest to rim 14 of vial 10, while the term "distal" denotes a distance furthest from the rim of the vial.

Figure 1:
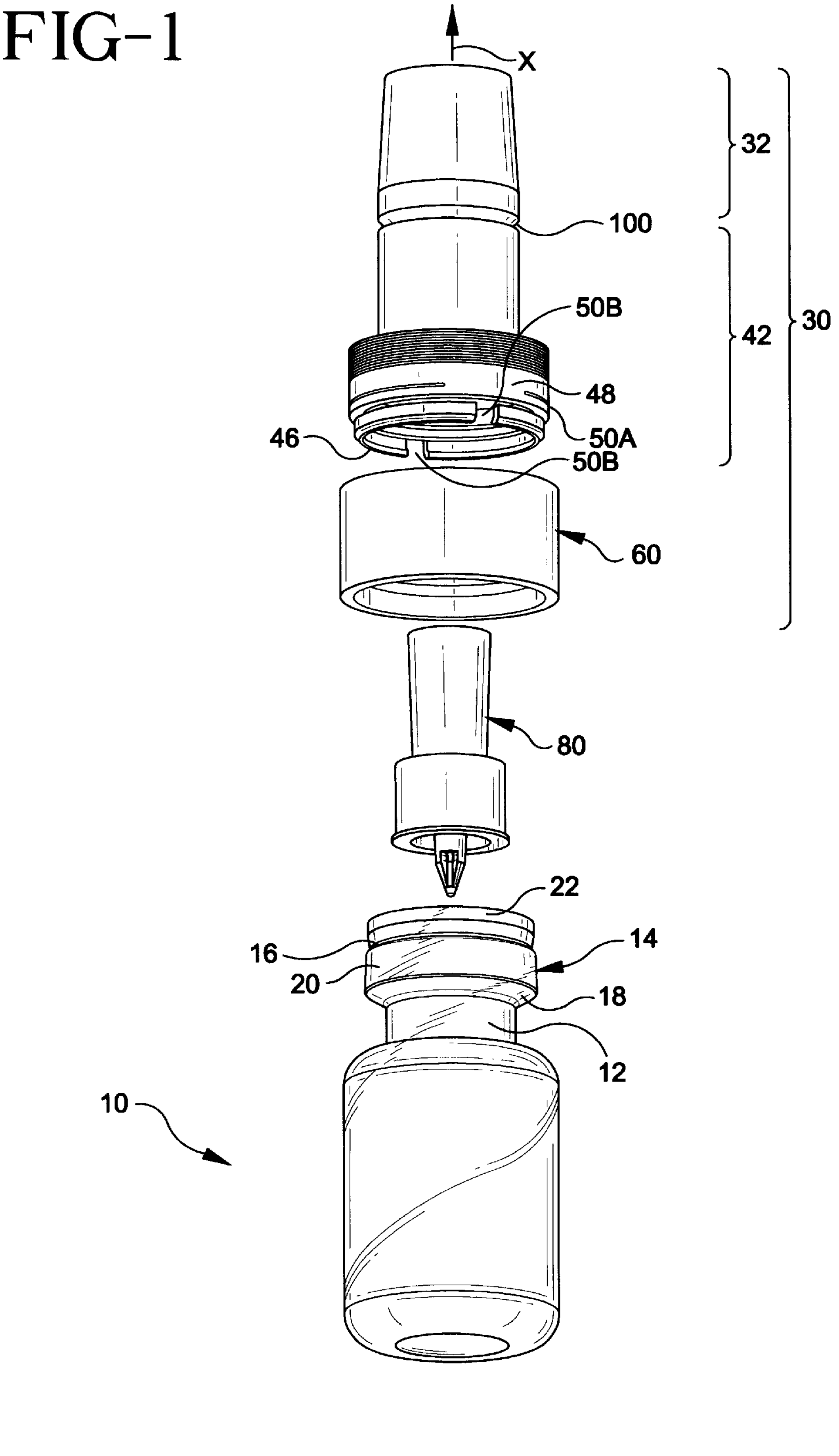
FIG. 1 is an exploded view of a first embodiment of the connector assembly in accordance with the present invention.
Figure 2:
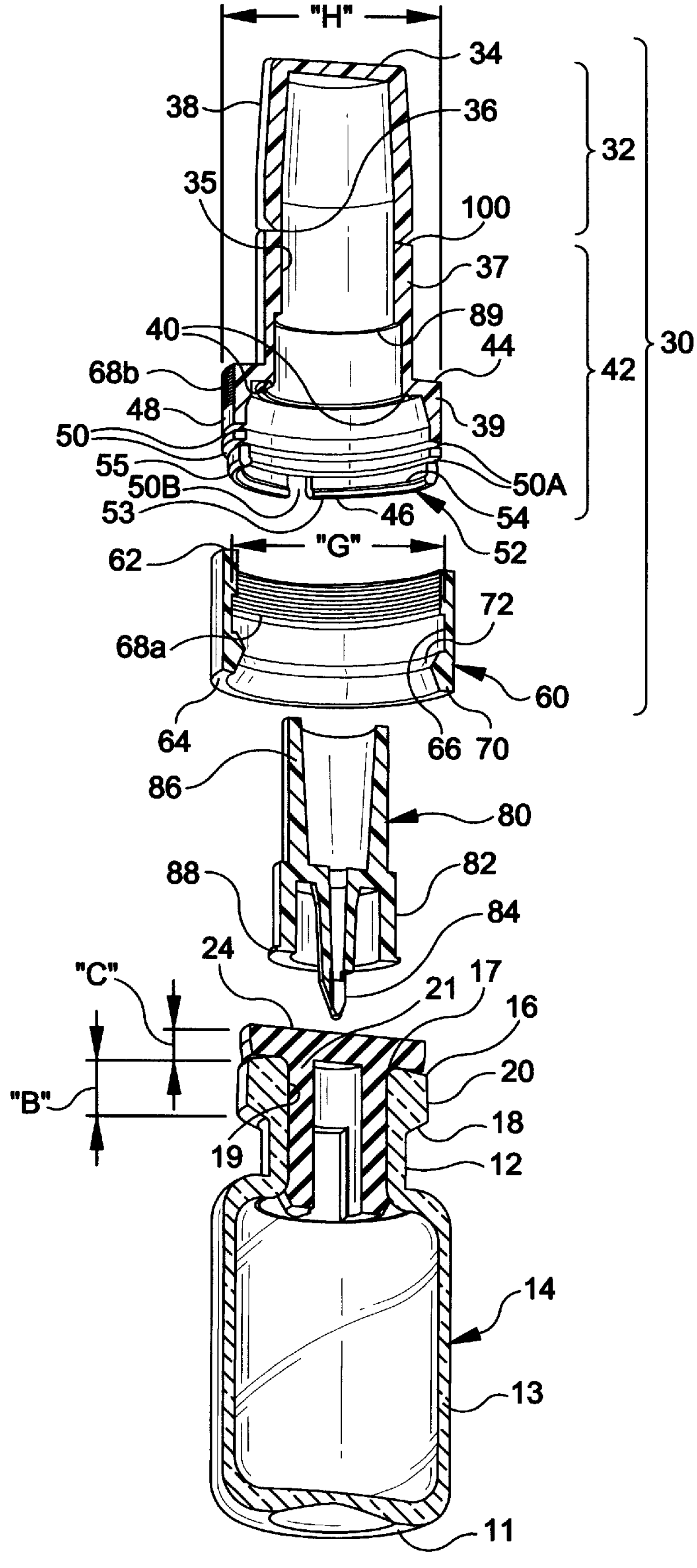
FIG. 2 is a cross-sectional view of FIG. 1.

Turning to the drawings, wherein like numerals denote like components, FIGS. 1 and 2 illustrate a first embodiment 30 of a connector assembly for a vial 10 in accordance with the present invention. Vial 10 is characterized by a bottom wall 11, a sidewall 13, a neck 12 and an annular rim 14. Annular rim 14 includes an underside portion 18, a side portion 20, and a top surface 16. A stopper 22 is typically employed to obturate an open end 17 associated with the vial. Stopper 22 features a planar portion 24 covering top surface 16 of the rim, and a plug portion 21 obturating the inside surface 19 of neck 12. Vial 10 is typically filled with a desired medicament, such as a dry drug or a lyophilized drug, and thereafter affixed with stopper 22, in a cleanroom environment. For the purposes of this invention, it will be realized that the dimensions and characteristics of vial 10 and stopper 22 can be conformed to various accepted standards, such as ISO standards, governing vials and stoppers intended for medicamental use.

As previously explained, a drawback in the art is ensuring that proper sealing forces exist between stopper 22 and vial 10. It would also be advantageous to incorporate a solution to this problem in a vial connector assembly that is easily processed by the pharmaceutical manufacturer and which, desirably, can be fully processed in the cleanroom environment where medicaments are processed, introduced into the vial, and stoppered within the vial.

With the foregoing in mind then, a first embodiment 30 of the connector assembly of the present invention is provided. Connector assembly 30 is formed of three principal components, namely, a cap 32, a collar 42, and a ring 60.

Cap 32 is characterized by a closed distal end 34, an open proximal end 36, and a shield wall 38 therebetween. Cap 32 is provided adjacent collar 42. Cap 32 and collar 42 can be formed together, such as by a co-injection process, or they can be separately formed and joined together by mechanical means, welding, or the like. In a preferred construction, cap 32 and collar 42 are formed together and connected by a frangible section 100, as will be hereinafter discussed.

Collar 42 is designed to mate with rim 14 of the vial. Collar 42 is located adjacent open proximal end 36. Collar 42 includes an upstanding tubular section 38 defining an interior portion 35. Interior portion 35 serves to engage a vial access device, as will be more fully explained hereinbelow. Adjacent tubular section 37 there is provided a vial attachment section 39. Vial attachment section 39 of the collar displays a distal end 44, an open proximal end 46, and a sidewall 48 therebetween. One or more sealing ribs 40 are provided, on an interior portion of vial attachment section 39, adjacent distal end 44. Ribs 40 can take any shape appropriate to their sealing function, such as rounded, peaked, square, or other geometries.

Figure 3:
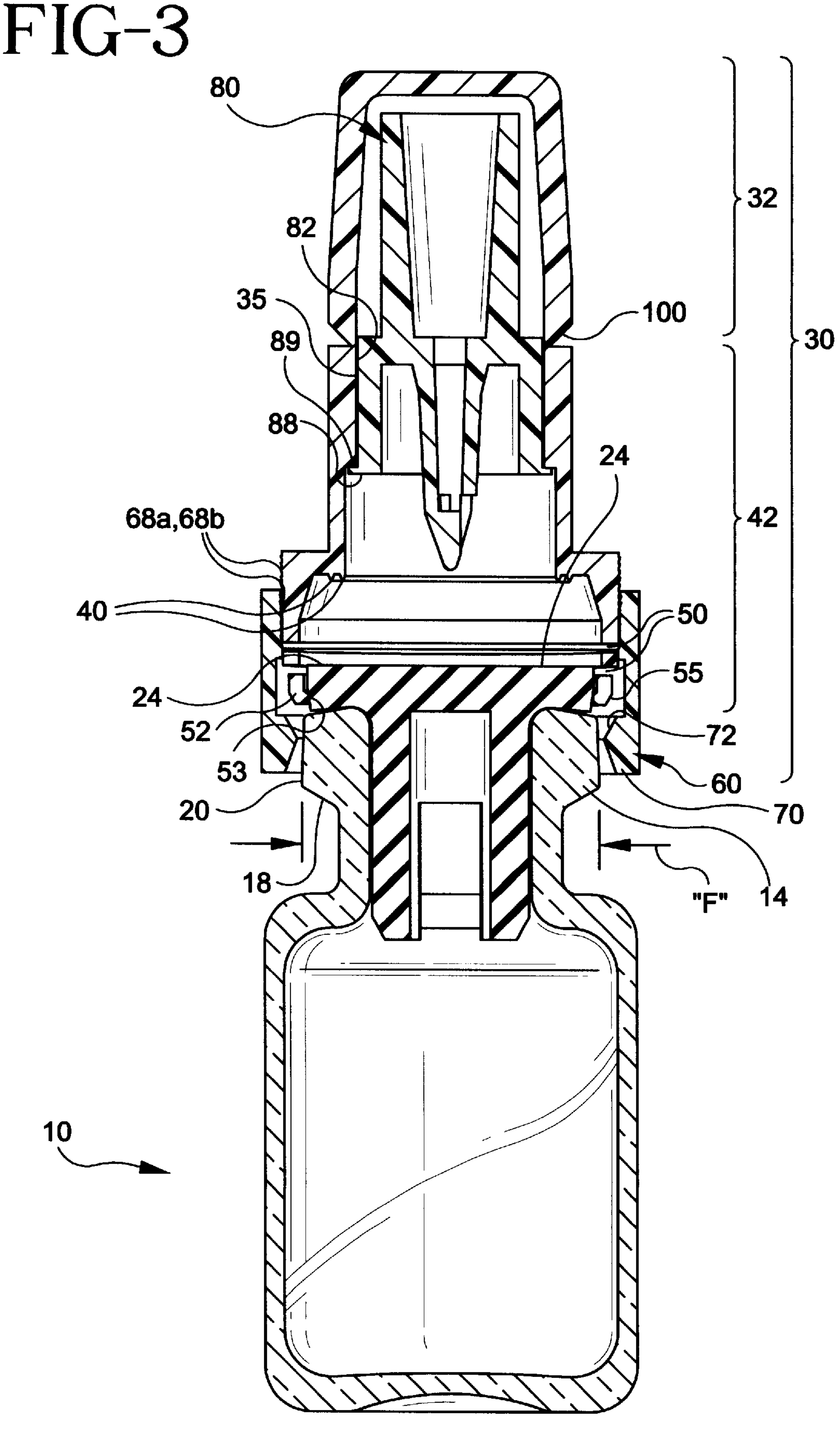
FIG. 3 is a cross-sectional view depicting placement of the connector assembly against the vial in a first position, wherein the collar is placed around the rim.
Figure 4:
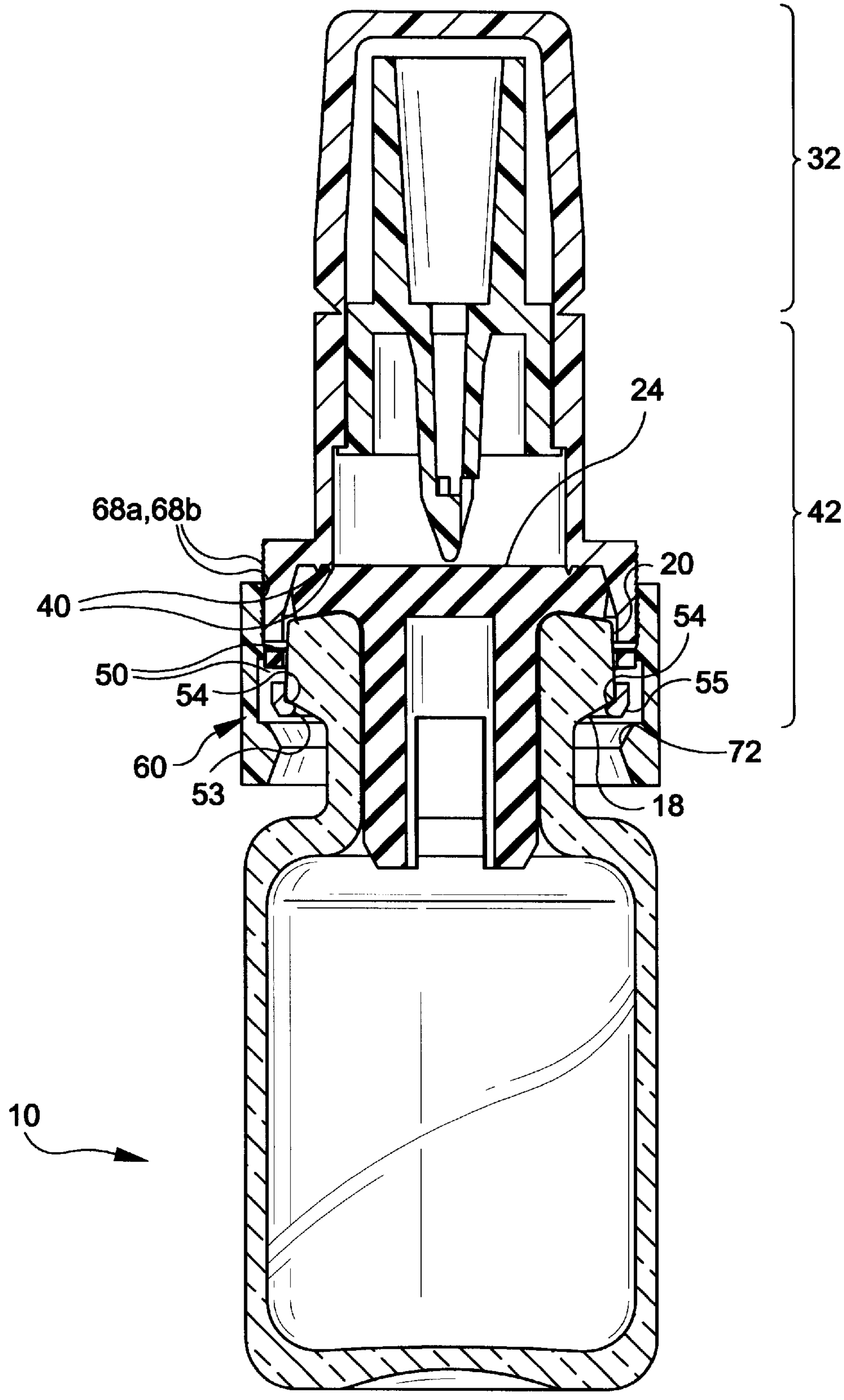
FIG. 4 is a cross-sectional view depicting placement of the connector assembly against the vial in a second position, whereby the latches provided on the collar are thrust against an underside portion of the rim.

One or more deflectable latches 52 are provided about the proximal end of collar 42. Deflectable latches 52 feature a proximally facing, outwardly canted surface 53 and a distally facing, inwardly canted surface 54. Outwardly canted surface 53 facilitates movement of collar 42 over the outside portion of rim 14 for movement of the collar from a first position, wherein sealing ribs 40 are spaced from planar portion 24 of stopper 22 (FIG. 3), to a second position, where sealing ribs 40 are engaged in surface contact with the planar portion of stopper 22 (FIG. 4). Inwardly canted surface 54 serves to lock the collar against underside portion 18 of the rim in the second position. In effect then, by properly configuring the dimensions of the various components, latches 52 of the collar will lock onto the underside of the rim, causing a sealing force to be applied by sealing ribs 40 against stopper 22.

Figure 7:
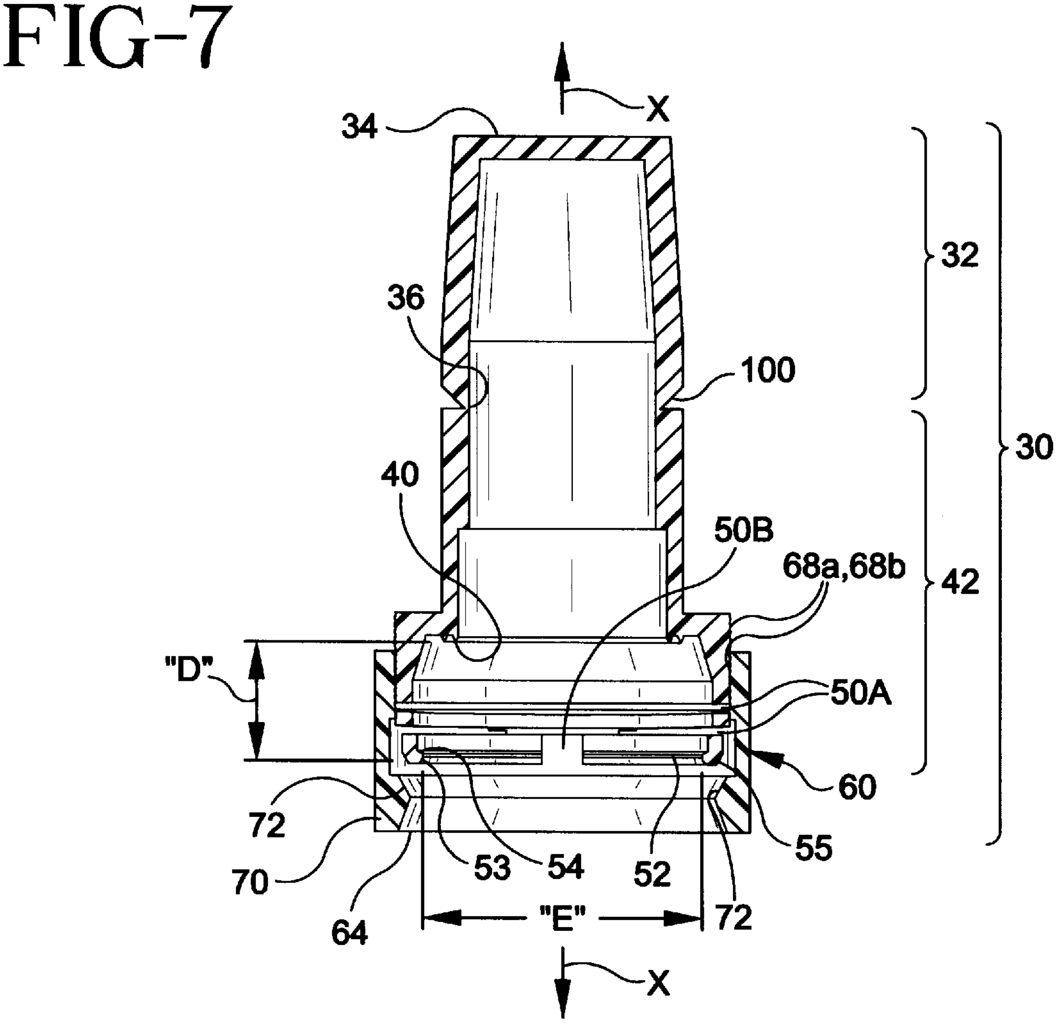
FIG. 7 is a cross-sectional view of the connector assembly.

A distinguishing feature of the collar is its ability to compensate for dimensional or tolerance variances between the stopper, the vial, or the connector assembly itself, so as to ensure that uniform sealing forces are applied over the surface of stopper 22. To this end, collar 42 is formed such that a plurality of slits 50A and 50B (collectively, slits 50) are disposed throughout sidewall 48 of the vial attachment section. Referring to FIGS. 1, 2 and 7, one or more slits 50A are formed in sidewall 48 in a direction radial to a central axis "X" defined by collar 42. As best seen in FIG. 1, slits 50A take the appearance of circumferential cuts about sidewall 48, and preferably, they do not extend about the entire circumference of sidewall 48. In addition, one or more slits 50B are formed in sidewall 48 in a direction parallel to central axis X. As best seen in FIG. 1, preferably, slits 50B are placed adjacent open proximal end 46 of the collar. The effect of slits 50 is to impart a degree of elasticity or flexibility to collar 42, allowing it to account for dimensional or tolerance variances in the various components.

For instance, the existence of slits 50A imparts a degree of flexibility to vial attachment section 39 of the collar in an axial direction parallel to central axis X. Thus, if for some reason the thickness "C" of planar portion 24 of the stopper or the thickness "B" of side portion 20 of the rim (FIG. 1) is not uniform, the vial attachment section of collar 42 can flexibly respond in an axial direction to account for those variances. That is to say, the distance measured between ribs 40 and inwardly canted surface 54—the two principal structures of collar 42 that engage stopper 22 and rim 14, respectively—will be adapted to the thicknesses "B" and "C" displayed by the rim and stopper, respectively. Similarly, slits 50B impart a degree of flexibility to the collar in directions radial to central axis X. Thus, for instance, if the shape of side portion 20 of the rim is not uniformly round, collar 32 may flexibly respond in a direction radial to central axis X to compensate. It is important to note, too, that the hardness displayed by the materials forming either of stopper 22 or vial 10 may affect the ultimate combined thicknesses "B" and "C'" of the rim and stopper and, thus, the sealing force ultimately exerted by ribs 40 against the stopper. Thus, the provision of slits 50 help to compensate for such variances as well. All in all, then, the sealing force imparted by ribs 40 will be constant from one connector assembly 30 to another.

Preferably, to ensure uniform sealing forces between the stopper and the rim, the collar is configured such that the height "D" (FIG. 7) between ribs 40 and inwardly canted distally facing surface 54 of the latches is at least equal to, if not slightly less, than the combined thickness B+C of rim 14 and planar portion 24 of the stopper, respectively, when collar 32 is in an unflexed condition. Similarly, inside diameter "E" measured between diametrically opposite latches 52 (FIG. 7) should be chosen such that it is at least equal to, or slightly less than, outside diameter "F" of rim 14 (FIG. 3) when the collar is in an unflexed condition. By unflexed condition, what is meant is that slits 50A are not compressed or expanded axially, and that slits 50B are not compressed or expanded radially, from their original configuration on sidewall 48.

Ring 60 is disposed about collar 32. Ring 60 serves to lock the collar to the rim in the second position. Ring 60 includes a proximal end 64, a distal end 62, and an annulus section 66 therebetween. Annulus section 66 preferably displays an inside diameter "G" at least equal to, if not slightly less than, outside diameter "H" of sidewall 48 (FIG. 2). Ring 60 includes an internally projecting rib 70 adjacent proximal end 64. An inwardly canted, distally facing locking surface 72 is provided on rib 70. Locking surface 72 is designed to mate with a cooperating outwardly-canted, proximally facing locking surface 55 provided on an exterior surface of latches 52 of the collar.

Figure 8:
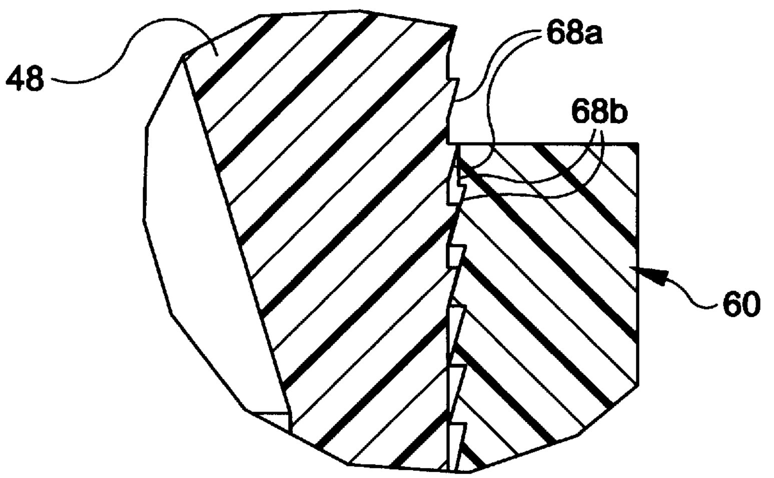
FIG. 8 is a cross-sectional view depicting locking structure provided between the ring and the collar.

Cooperating locking structure is provided between the ring and the collar. This locking structure, denoted by numeral **68*b* for the collar and numeral 68*a* for the ring, can be structured in a variety of manners. Referring to FIGS. 2 and 8, locking structure 68*a* and 68*b* can take the form of cooperating ratcheting teeth formed about the respective circumferences of sidewall 48 of the collar (68*b*) and annulus section 66 of the ring (68***a*). Each of the sets of ratcheting teeth are placed adjacent the respective distal ends 62, 44 of the ring and collar, respectively. Alternate structure can also be envisioned for the locking structure. For instance, cooperative threads can be substituted for the ratcheting teeth. Other structure within the realm of the skilled artisan is also possible.

Connector assembly 30 typically encloses a vial access device 80. Vial access device 80 is structured to pierce stopper 22 so as to gain access to the medicament held by vial 10. While not limited in scope, in general vial access device 80 may feature a body 82 in frictional engagement with an interior surface 35 associated with tubular section 37 of the collar. A distally facing piercing element 84 is mounted to the body. A connector end 86, attached in fluid communication to piercing element 84, is provided to mount the vial access device to an external component such as a syringe, a rigid bottle, a flexible bottle, or the like. It will be realized by the skilled artisan that piercing element 84 can take various configurations, such as a pointed metallic or plastic needle, a spike, or any pointed structure serving to pierce stopper 22. Similarly, connector end 86 can be configured as a spike, a needle, as a luer connector, or any other desirable configuration to mate with the various external components, such as rigid fluid bottles, luer lock or luer slip syringes, flexible fluid bags, or the like, with which an end user will want to employ with the connector assembly.

Operation of the connector assembly will now be explained, referring principally to FIGS. 3–6.

In practice, the pharmaceutical customer would process or otherwise fill a desired medicament in vial 10, thereafter applying stopper 22 to the vial neck. Both of these operations would occur in a cleanroom environment. As illustrated in FIG. 3, the component manufacturer would normally supply connector assembly 30 to the pharmaceutical manufacturer in a pre-assembled sterile state, ready to apply to an already stoppered vial.

As illustrated in FIG. 3, in the pre-assembled state, ring 60 is positioned about collar 42 such that ring 60 is in an unlocked position respective of the collar. That is to say, proximal end 64 of the ring is displaced proximally way from proximal end 46 of the collar, such that locking surface 72 of internally projecting rib 70 on the ring is displaced from contact with outwardly canted surface 55 of latches 52. Latches 52 are thus free to flex respective of sidewall 48, particularly along slits 50A, SOB. Locking structure 68*a*, 68*b* retains the ring to the collar. Vial access device 80 is enclosed inside cap 32 and collar 42. Pre-assembled connector assembly 30 is thus placed over vial 10 directly in the cleanroom, with open proximal end 64 of the ring passing around side portion 20 of rim 14. It will also be seen that outwardly facing, proximally directed surface 53 of the latches have engaged against the periphery of planar portion 24 of the stopper at this time.

FIG. 4 illustrates placement of the connector assembly in its second position relative to vial 10. Here, outwardly facing, proximally directed surfaces 53 have been urged over outside portion 20 of the rim, and inwardly facing, proximally directed surfaces 54 of the latches have engaged underside 18 of the rim. At the same time, ribs 40 provide adjacent distal end 44 of cap 42 have descended upon stopper 22 such that they are engaged in tight sealing contact with planar portion 24. At this time also, ring 60 continues to be displaced in an unlocked position relative to collar 42. Note that ring 60 continues to be located in an unlocked position relative to collar 42. Thus, as the collar is displaced to its second position relative to the vial rim, the sidewall can flex both radially and axially to accommodate any dimensional or tolerance variances, as previously described. Equal forces will be exerted by the collar across the surface of the stopper, ensuring a proper seal between the stopper and the vial.

Figure 5:
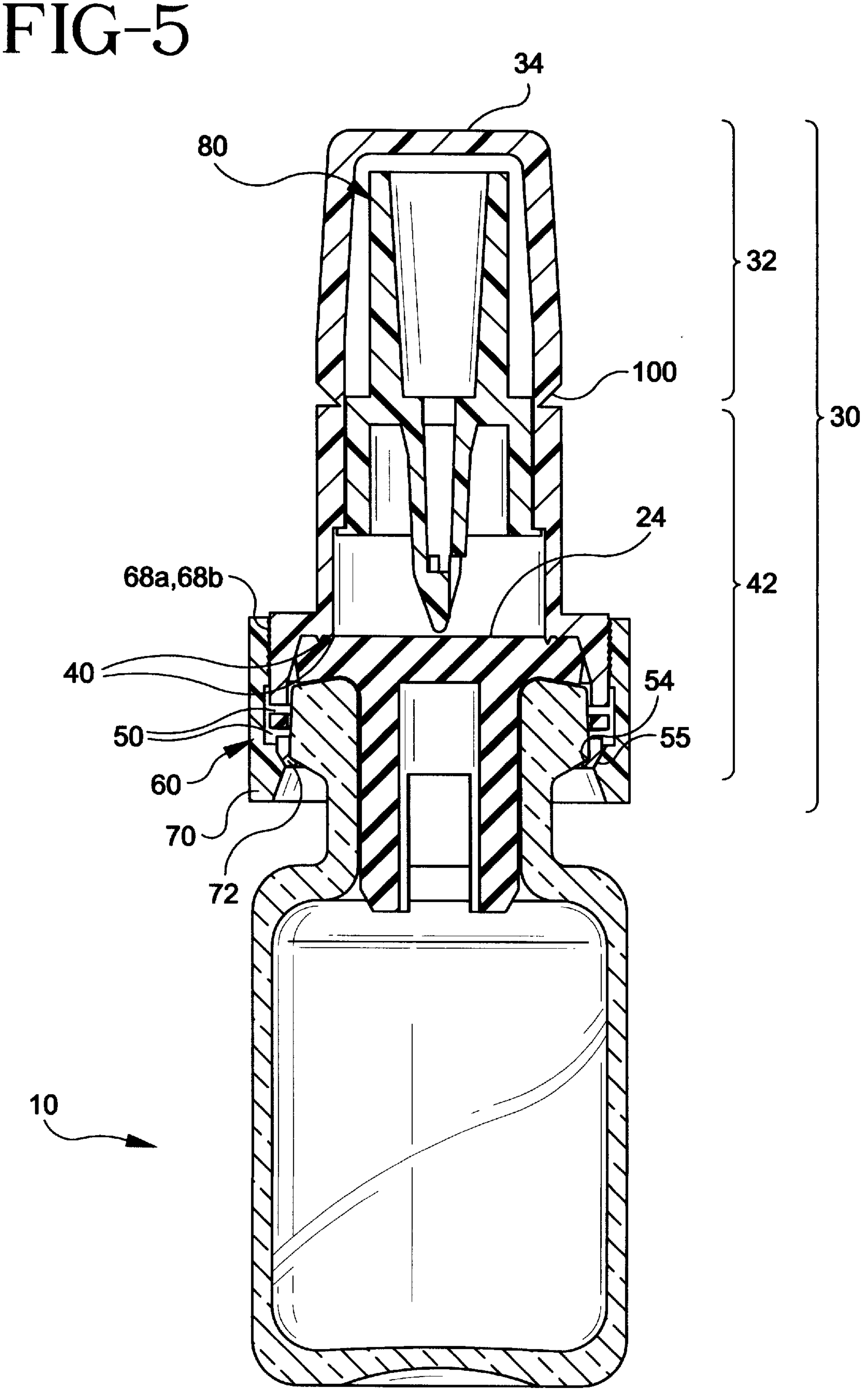
FIG. 5 is a cross-sectional view depicting movement of the ring to a locked position respective of the collar.

Once the connector assembly has been urged to the second position such that it has locked against the rim and a seal has been formed between ribs 40 and planar portion 24 of the stopper, the connector assembly and vial can be removed from the cleanroom environment for the final assembly step, represented by FIG. 5. Of course, it will be understood that this step can take place in the cleanroom, if desired. In FIG. 5, ring 60 is displaced distally respective of collar 42 until a locked position is reached. In the embodiment shown, ratcheting teeth 68*b* of the ring are displaced distally of ratcheting teeth 68*a* of the collar, until such time as locking surface 73 of internally projecting rib 70 of the ring presses tightly against outwardly canted surface 55 of latches 52, and inwardly canted, proximally facing surface 54 mates tightly with underside portion 18 of the rim. Continued distal displacement of the ring relative to the collar also causes ribs 40 to bite tightly into planar portion 24 of the stopper, thereby ensuring a good microbiological seal between the ribs and the stopper. At the same time, stopper 22 is also pressed into good sealing contact with rim 14, ensuring a good microbiological seal between the two. The effect is that two microbiological barriers are created—one between the sealing ribs and the planar portion of the stopper, and one between the planar portion of the stopper and upper surface 16 of the rim—in a unform manner across the entire planar portion of the stopper. Vial access device 80 is thus secured in microbiological isolation within connector assembly 30, and stopper 22 tightly sealed to vial 10 so as to isolate the drug held by the vial. Locking structure 68*a*, 68*b* between the ring and the collar will retain the two in locked position. Connector assembly 30 is now securely affixed to the vial, and the pharmaceutical manufacturer may ship the filled vial to the end user.

Figure 9A:
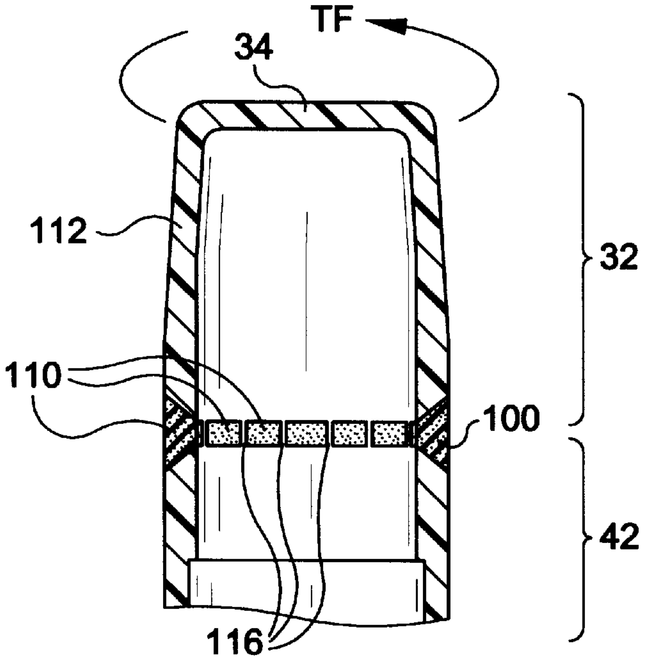
FIGS. 9A and 9B depict two manners of configuring a frangible section between the cap and the collar to permit removal of the cap from the collar to expose the vial access device.
Figure 9B:
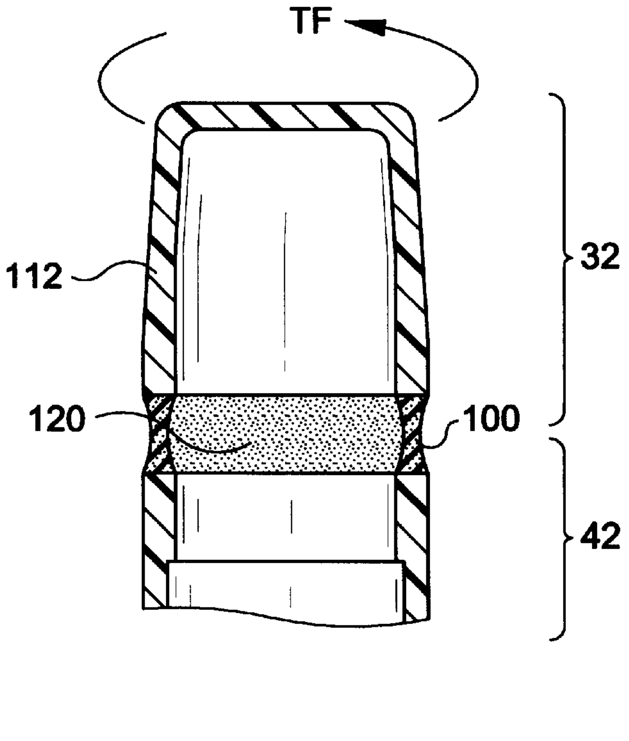

To employ the vial, cap 32 must be removed from collar 42 so as to expose vial access device 80. While various ways can be configured to so remove the cap, FIGS. 9A and 9B illustrate forming cap 32 and collar 42 together and connecting them by a frangible section 100. Frangible section 100 permits a user to apply a twisting force to cap 32 so as to remove the cap from the collar to expose vial access device 80. Cap 32 and collar 42 may be formed together by a co-injection process, wherein a material having a low shear resistance is employed for frangible section 100, and a material having a higher shear resistance is employed for the rest of the cap and the collar. For instance, frangible section 100 can be formed by employing various thermoplastic elastomers ("TPE") displaying low shear resistance, and which display good adhesion properties to the material chosen for the rest of the cap, which typically can be polypropylene or polyethylene.

As illustrated in FIG. 9A, frangible section 100 can be configured as a series of TPE pockets, or "teeth", 110 that are molded into an interior section 112 defined between cap 32 and collar 42. Teeth 110 are interspersed with intervening sections 116 of the section 100, the intervening sections formed from the more shear resistant material that makes up the remainder of cap 32 or collar 42. The resulting frangible section 100 allows a user to exert a moderate twisting force "TF" against the cap to remove it. At the same time, the presence of intervening sections 116 strengthen the frangible section against inadvertent removal of the cap caused, for instance, by jostling during shipment, inadvertent opening by an end user, or the like. Alternately, as illustrated in FIG. 9B, if desired, frangible section 100 can be formed as a solid section 120 of TPE material across interior section 112. In any event, by forming cap 32 and collar 42 as a single unit, an additional, portential area for microbiological contamination—the juncture between the cap and the collar—is eliminated, leading to a concomitant reduction in the number of microbiological barriers needed.

It will also be realized that cap 32 and collar 42 can be formed separately and attached by various means, such as by welding, adhesives, or the like. That will safeguard integrity of the connection between the cap and the collar, but that will provide a reasonable force to permit a user to remove the cap.

Figure 6:
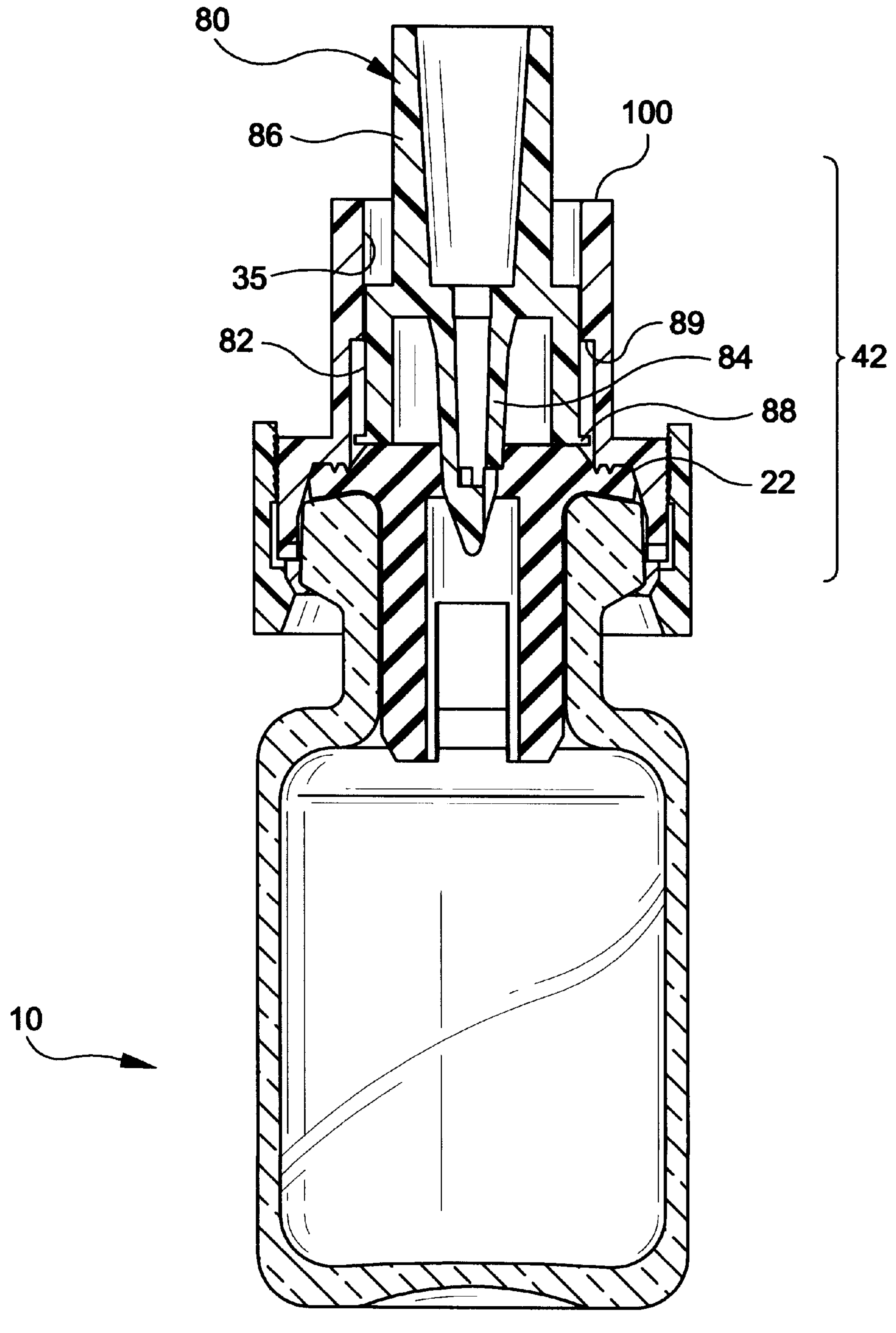
FIG. 6 is a cross-sectional view depicting the cap removed from the collar to expose the vial access device, and the subsequent actuation of the vial access device against the stopper.

In use then, cap 32 is removed from collar 42, and vial access device 80 exposed. FIG. 6 illustrates activation of the vial access device. An external component (not shown) is attached to connector end 86, and a proximally directed force applied. Piercing element 84 is urged through stopper 22 and in communication with the interior of the vial. Body 82 is slidably disposed with respect to interior surface 35 of shield wall 38. The engagement between body 82 and interior surface 35 can be by frictional engagement, via mechanical engagement such as by threaded engagement or by a lot and follower arrangement, or by other arrangements within the realm of the skilled artisan. If desired, body 82 can be retained against inadvertent removal from shield wall 38 by providing a stop 88 adjacent a proximal end of body 82 that is arrested by a shoulder 89 inside shield wall 38.

Figure 10:
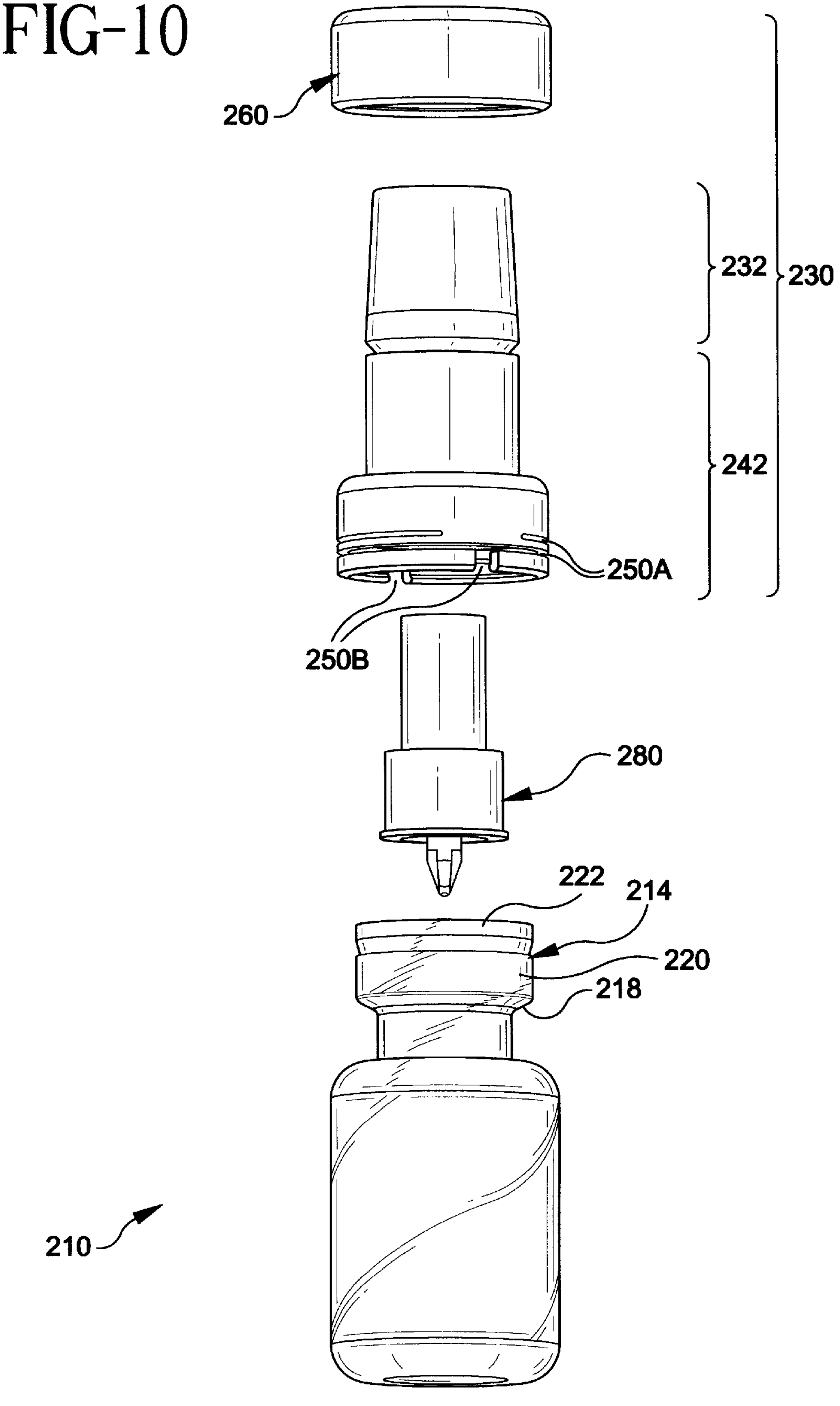
FIG. 10 is an exploded view of a second embodiment of the connector assembly in accordance with the present invention.
Figure 11:
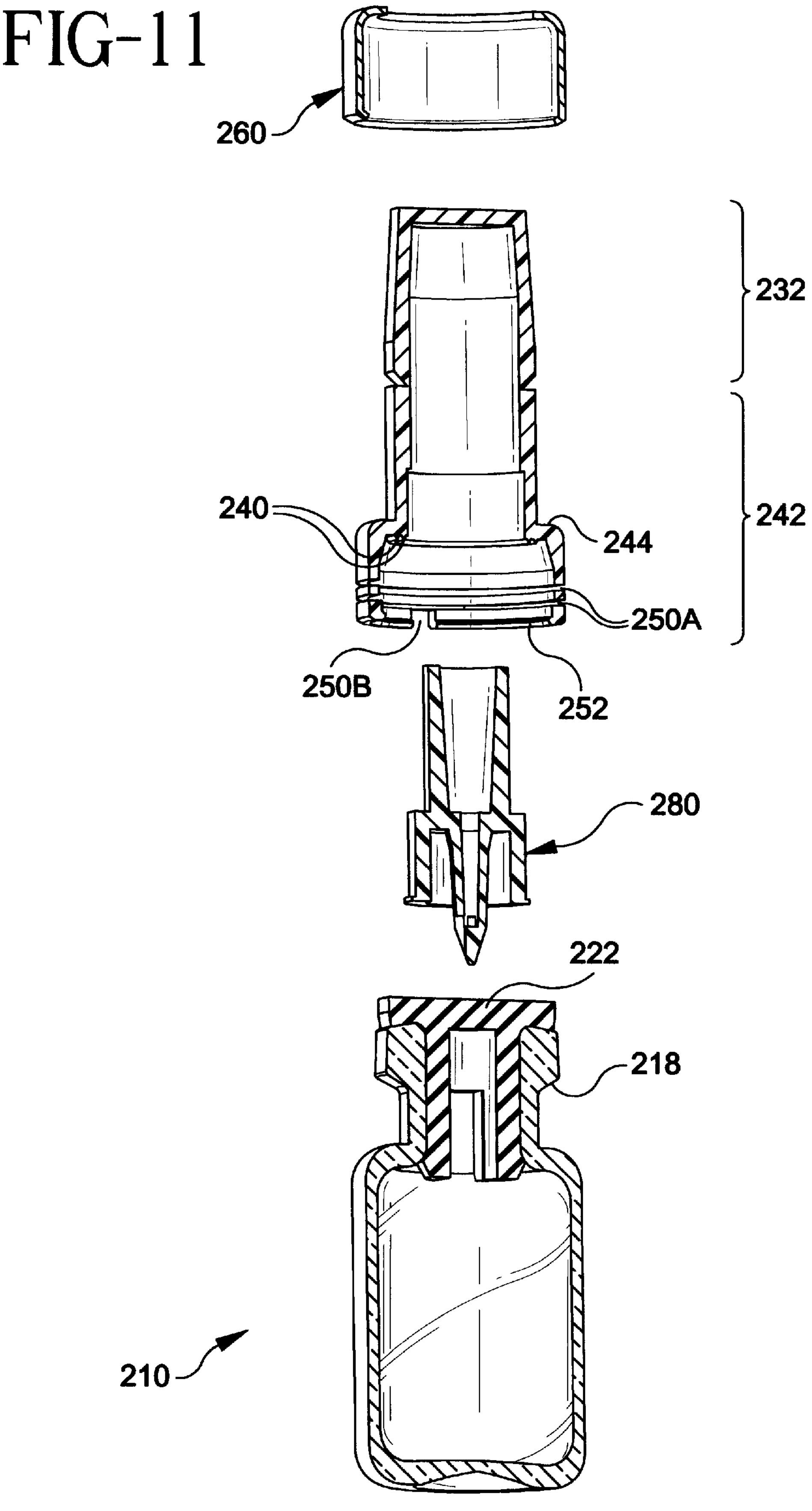
FIG. 11 is a cross-sectional view of FIG. 10.
Figure 12:
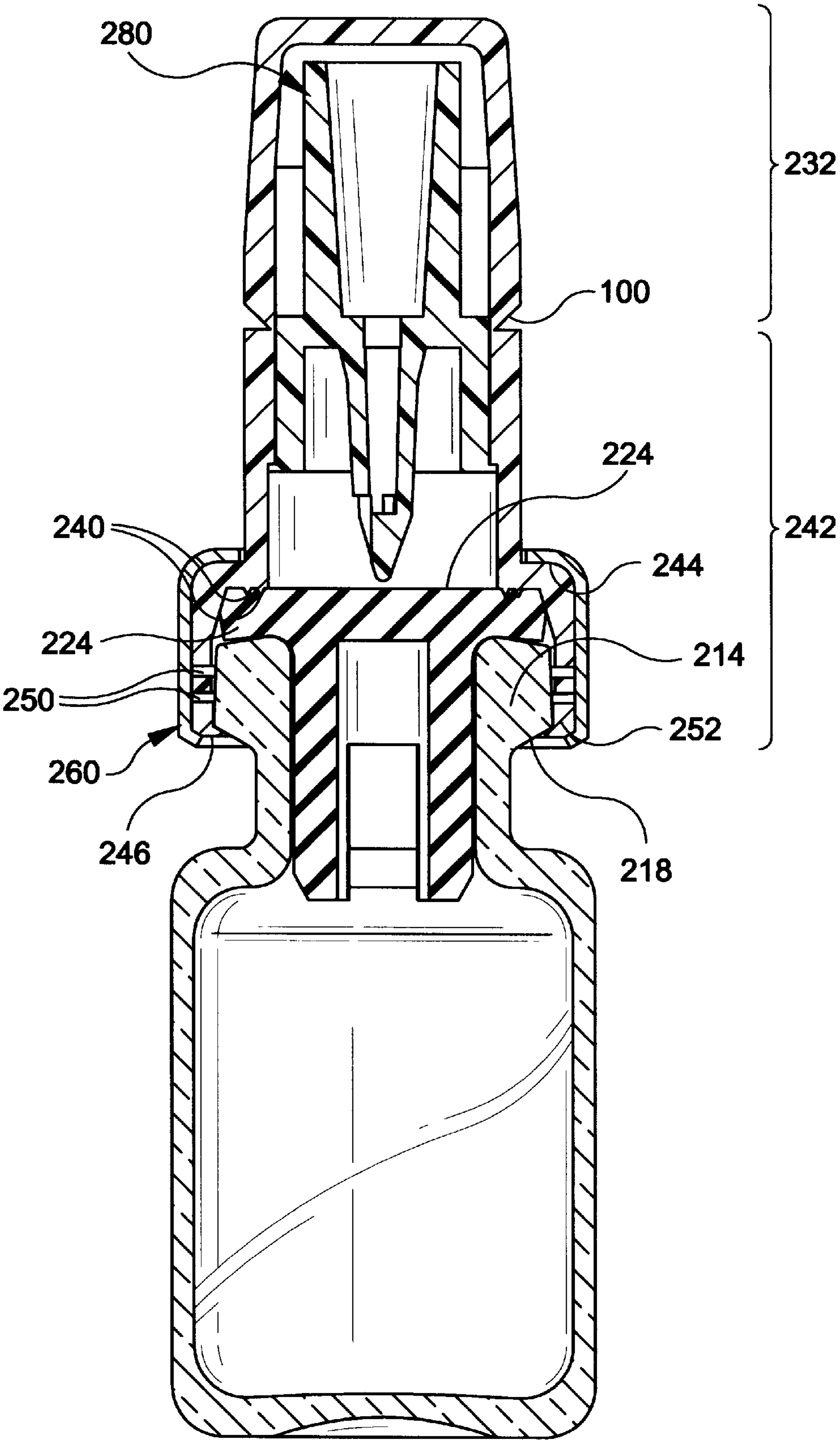
FIG. 12 is a cross-sectional view depicting placement of the connector assembly of FIGS. 10 and 11 against the vial rim.

FIGS. 10–12 illustrate a second embodiment 230 of a connector assembly in accordance with the present invention. In describing this embodiment, like components are described as for the embodiment of FIGS. 1–5 above, except that a prefix "2" is supplied to the numerical designation for those components. Accordingly, detailed description of those like components need not be repeated for embodiment 230.

Here, connector assembly 230 is substantially as before described, except that the ring 60 of the prior embodiment 30 is replaced by a conventional aluminum crimp cap 260. Cap 232 and collar 242 are formed as their counterparts in embodiment 30, except that locking structure 68*a* is omitted from the collar as no ring is required.

As before, connector assembly 230 is supplied to a pharmaceutical manufacturer in a pre-assembled, sterile state, with vial access device 280 engaged in the interior of shield 232. In the confines of the cleanroom, collar 242 is placed in one operation over vial rim 214, such that latches 252 engage underside 218 of the vial rim. Ribs 244 engage planar portion 224 of the stopper to form a tight seal, with collar 242 flexibly accommodating the stopper and rim via slits 250A, 250B. Thereafter, with the connector assembly attached to the vial in a sealing manner, the connector assembly and vial can be removed from the cleanroom so that crimp cap 260 can be applied about distal end 244 and proximal end 246 of the collar, locking the collar to the vial. As before a frangible section (here again denoted by numeral 100) can be incorporated between cap 232 and collar 242.

If desired, the connector assembly can be supplied with crimp cap 260 pre-attached to collar 242 in an uncrimped condition, such that connector assembly 230 together with the uncrimped crimp cap 260 are applied to the vial in the cleanroom, and the ribs 240 urged into sealing relation with stopper 222. Thus, the only operation which need occur outside of the cleanroom is the actual crimping operation.

The various components can be constructed from materials standard in the art. For example, the cap, the collar, and the ring can be injection molded from various thermoplastics (the construction of the frangible section having been already explained). The vial access device can be made from various medical grade plastics, medical grade stainless steels, combinations of these materials, or the like. Various rubbers or elastomers can be chosen for the stopper, and the vial can be made from suitable glass or plastics materials adapted to the drug held therein. If desired, various tamper evidence means, such as heat shrunk plastic strips, can be incorporated between the vial and the collar.

It will be appreciated and understood by those skilled in the art that further and additional forms of the invention may be devised without departing from the spirit and scope of the appended claims, the invention not being limited to the specific embodiments shown.

We claim:

1. A connector assembly for a vial, said vial including a neck, an open end at the proximal end of the neck, a rim bounding the open end, and a stopper obturating the open end of the vial, the rim having a side portion and an underside facing away from the open proximal end of the vial, the stopper having a planar portion covering the rim, the connector assembly comprising:

a protective cap for covering the open end of the vial, the cap comprising an open proximal end, a closed distal end, and a shield wall formed therebetween;

a collar provided adjacent the open proximal end of the protective cap, the collar having a proximal end, a distal end, and a sidewall therebetween, the collar movable between a first position wherein the distal end of the collar is spaced from the stopper, and a second position, wherein the distal end of the collar engages the planar portion of the stopper; one or more slits being defined in the sidewall to permit flexibility of the collar in axial and radial directions with respect to the neck of the vial, and one or more deflectable latches provided about the proximal end of the collar, each of the latches including locking means deflectable about the side portion of the rim for secured engagement with the underside of the rim when the collar is in the second position;

a crimp cap affixed about the sidewall of the collar, the crimp cap applying a force to the proximal and distal ends of the collar to lock the collar to the rim of the vial;

said locking means including an inwardly directed locking surface on said latch and an outwardly directed surface on said latch in functional relation with said crimp cap; and wherein when said crimp cap is applied to the collar, an inwardly-directed force is transmitted to said latch to retain the locking surface in secured relation with the underside of said rim.

2. The connector assembly of claim 1, further comprising a vial access device having a piercing element for piercing the stopper.

3. The connector assembly of claim 2, wherein the vial access device is engaged against an interior portion of the collar.

4. The connector assembly of claim 1, wherein the cap is integrally formed with the collar.

5. The connector assembly of claim 4, wherein the cap and the collar include a frangible section between them to enable a user to remove the cap from the collar.

6. The connector assembly of claim 5, wherein the cap and the collar are molded from a material selected from the group comprising polypropylene or polyethylene, and the frangible section is formed from a thermoplastic elastomer.

7. The connector assembly of claim 1, wherein the cap is affixed to the collar by adhesives or welding, wherein the cap is formed from a material selected from the group comprising polyethylene or polypropylene.

8. The connector assembly of claim 1, further comprising a vial access device having: a body engageable with an interior portion of the collar; a piercing element for piercing the stopper on the vial; and a connector end in fluid communication with the piercing element to connect the vial access device to an external component.

9. The connector assembly of claim 8, wherein the connector end of the vial access device is selected from the group comprising a luer connector, a spike, or a needle.

10. The connector assembly of claim 1, wherein the crimp cap is pre-affixed to the collar in an uncrimped condition.

* * * * *